US009791397B2

(12) United States Patent
Deschler et al.

(10) Patent No.: US 9,791,397 B2
(45) Date of Patent: Oct. 17, 2017

(54) DEVICE FOR DETECTING CONTACT OF AN ELECTRICAL CONDUCTOR BY A TOOL

(71) Applicant: SCHLEUNIGER HOLDING AG, Thun (CH)

(72) Inventors: Raphael Deschler, Oberhofen (CH); Michael Jost, Thun (CH); Roland Kampmann, Witten (DE); Martin Thiele, Radevormwald (DE)

(73) Assignee: Schleuniger Holding AG, Thun (CH)

( * ) Notice: Subject to any disclaimer, the term of this patent is extended or adjusted under 35 U.S.C. 154(b) by 200 days.

(21) Appl. No.: 14/778,092

(22) PCT Filed: Mar. 21, 2014

(86) PCT No.: PCT/IB2014/060038
§ 371 (c)(1),
(2) Date: Sep. 20, 2015

(87) PCT Pub. No.: WO2014/147596
PCT Pub. Date: Sep. 25, 2014

(65) Prior Publication Data
US 2016/0054251 A1 Feb. 25, 2016

(30) Foreign Application Priority Data

Mar. 21, 2013 (EP) .................... 13160497

(51) Int. Cl.
*G01N 27/22* (2006.01)
*H02G 1/12* (2006.01)
*H01H 1/00* (2006.01)

(52) U.S. Cl.
CPC ......... *G01N 27/228* (2013.01); *H02G 1/1248* (2013.01); *H02G 1/1253* (2013.01); *H01H 1/0015* (2013.01)

(58) Field of Classification Search
CPC .. G01N 27/228; H02G 1/1248; H02G 1/1253; H01H 1/0015
See application file for complete search history.

(56) References Cited

U.S. PATENT DOCUMENTS 4,185,522 A 1/1980 Reinertz et al.
4,639,824 A 1/1987 Furlong et al.
(Continued)

FOREIGN PATENT DOCUMENTS

DE 3426322 C2 1/1986
DE 4025380 C1 10/1991
(Continued)

OTHER PUBLICATIONS

Article titled "Smarter Sensor meistert alle Anwendungen ," in Sensor Magazin, vol. Jan. 2006, pp. 30-33, in German, translation to English attached.

(Continued)

*Primary Examiner* — Robert Scruggs
(74) *Attorney, Agent, or Firm* — Davis & Bujold PLLC; Michael J. Bujold

(57) ABSTRACT

The invention relates to a device for detecting contact of a tool (2a, 2b) with an electrical conductor (5b) encased by an electrical insulation (5a).
In order to ensure a reliable, robust and simple display of the tool-conductor contact for potential-free and short cable lengths, the tool (2a, 2b) consisting of an electrically conductive material is fastened to a tool holder (1a; 1b) made of electrically conductive material. A thin electrical insulation is provided between tool (2a, 2b) and tool holder (1a, 1b) so that these components together with the coaxial cable form a capacitor (CS).
An inductance (La; Lb) is connected parallel to this so that a high-Q LC resonant circuit is formed between tool and tool (Continued)

Figure 1:
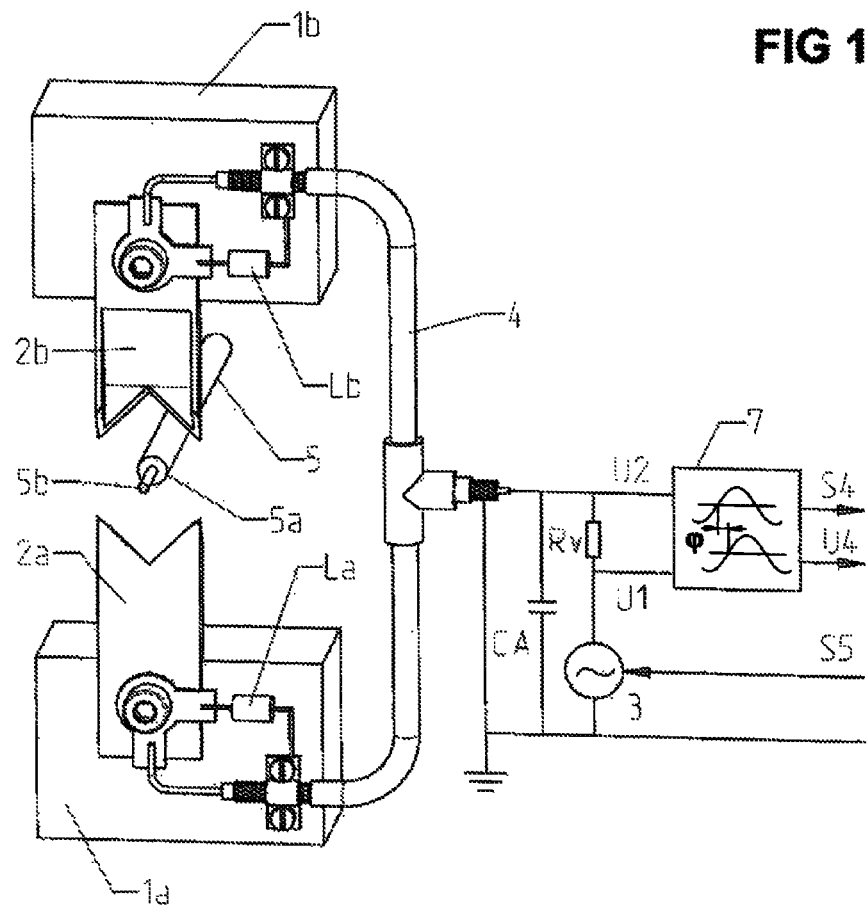

holder. The electronic circuit arrangement excites the resonant circuit and determines characteristic oscillation parameters of this resonant circuit.

Furthermore, for the cable processing tool-conductor contacts can be weighted according to contact time and specific time within the cable processing process and thus quantitative production exclusion criteria are determined.

16 Claims, 7 Drawing Sheets

(56) References Cited

U.S. PATENT DOCUMENTS

| | | | |
|---|---|---|---|
| 4,679,117 | A | 7/1987 | Butcher et al. |
| 4,682,272 | A | 7/1987 | Furlong et al. |
| 5,111,720 | A | 5/1992 | Stepan |
| 5,272,941 | A | 12/1993 | English et al. |
| 5,727,409 | A | 3/1998 | Inoue et al. |
| 6,324,945 | B1 | 12/2001 | Lo et al. |
| 6,505,399 | B2 | 1/2003 | Lo et al. |
| 7,432,725 | B2 | 10/2008 | Sieh et al. |
| 9,032,842 | B2 * | 5/2015 | Hombu ............... H01R 43/28 81/9.4 |
| 2007/0121796 | A1 | 5/2007 | Lurati et al. |
| 2008/0100146 | A1 | 5/2008 | Washington |
| 2010/0251857 | A1 | 10/2010 | Whittaker et al. |
| 2011/0062960 | A1 | 3/2011 | Prakash et al. |

FOREIGN PATENT DOCUMENTS

| | | |
|---|---|---|
| DE | 4215163 A1 | 11/1993 |
| DE | 19903194 A1 | 8/2000 |
| DE | 102007053825 A1 | 5/2009 |
| DE | 102009027967 A1 | 2/2010 |
| DE | 202011107872 U1 | 2/2013 |
| EP | 1772701 B1 | 5/2008 |
| EP | 2299459 A1 | 3/2011 |
| JP | H02-133016 A | 5/1990 |
| JP | H06-347429 A | 12/1994 |
| JP | H07-227022 A | 8/1995 |
| JP | H07-236214 A | 9/1995 |
| JP | H10-112913 A | 4/1998 |
| JP | H11-299036 A | 10/1999 |
| JP | 2000-354315 A | 12/2000 |
| WO | 01/88583 A1 | 11/2001 |
| WO | 2011/111238 A1 | 9/2011 |
| WO | 2012/015062 A1 | 2/2012 |

OTHER PUBLICATIONS

PCT International Preliminary Report on Patentability, Chapter II PCT, parent application PCT/IB2014/060038, dated Jul. 2, 2015, with full English translation.

International Search Report and International Preliminary Report on Patentability, dated Jun. 25, 2014, from parent application PCT/IB2014/060038; with partial English translation.

EPO search report and written opinion from priority EPO application EP13160497, dated Jun. 19, 2013, in German.

Article titled, "Smarter Sensor meistert alle Anwendungen ," in Sensor Magazin, vol. 1/2006, pp. 30-33, in German.

* cited by examiner $$Z_L = Rk + sL$$

$$Z_C = Rd + \frac{1}{sC}$$

$$Z_C = \frac{1 + sRdC}{sC}$$

$$H(s) = \frac{Rk + s(L + RkRdC) + s^2 RdLC}{(Rv+Rk) + s(L+RvC(Rk+Rd) + RkRdC) + s^2 LC(Rv+Rd)}$$

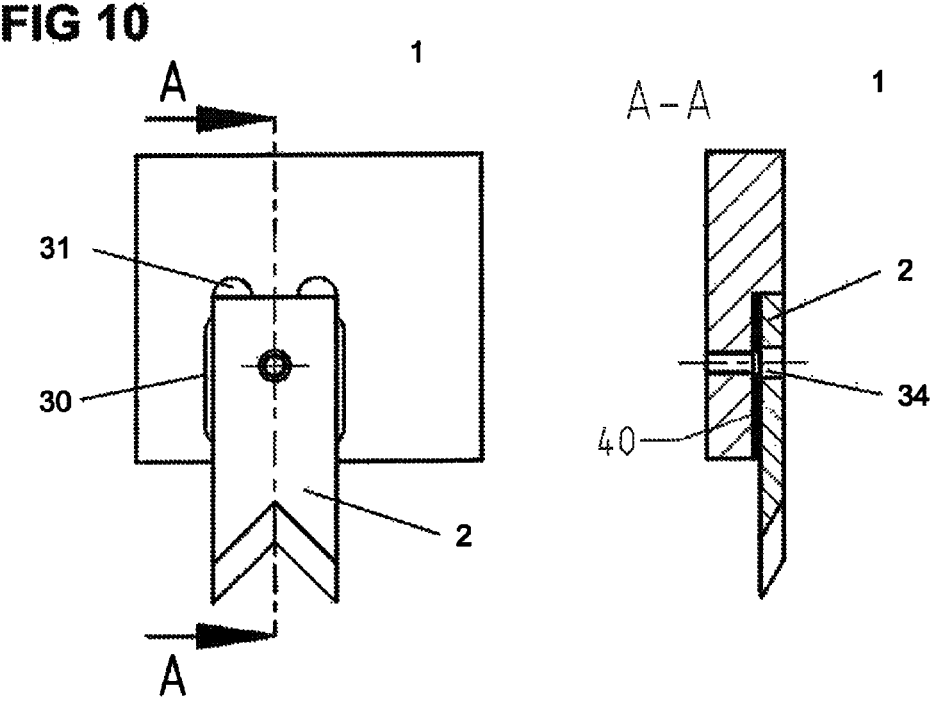
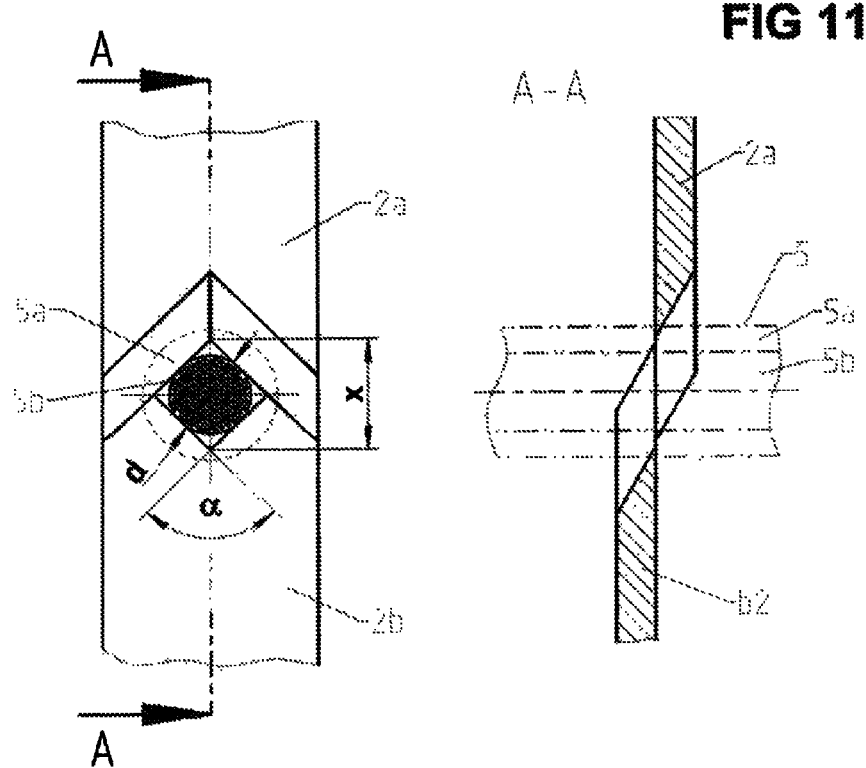

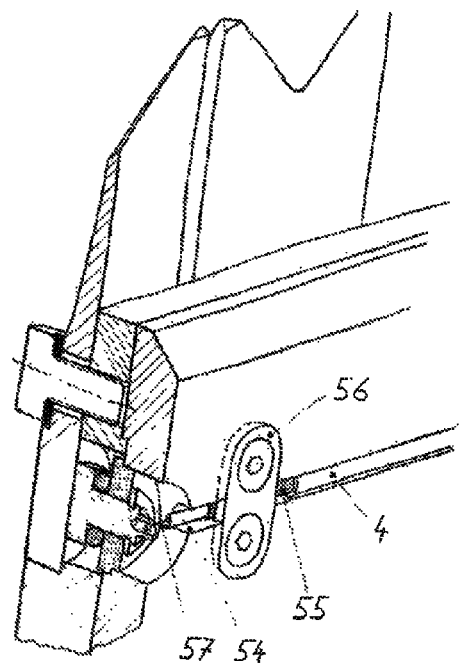
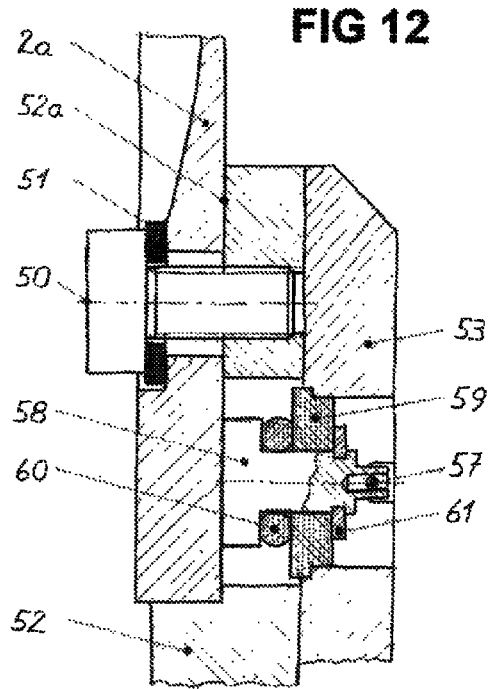
FIG 12
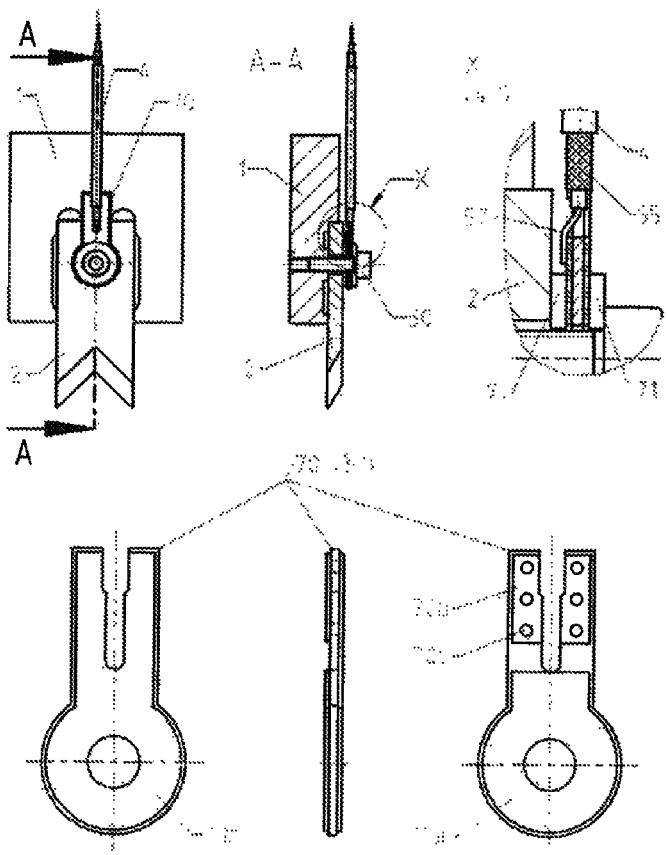
FIG 13

DEVICE FOR DETECTING CONTACT OF AN ELECTRICAL CONDUCTOR BY A TOOL

The invention relates to a device for detecting contact of an electrical conductor optionally encased by a mostly electrical insulation by a tool which consists of an electrically conductive material and which is fastened to a tool holder made of electrically conductive material, wherein a thin electrical insulation is provided between tool and tool holder according to the preamble of claim 1 as well as a stripping machine having at least one stripping blade which is held on a tool holder and having a device for detecting contact of an electrical conductor of a cable by at least one of the stripping blades according to the preamble of claim 16.

When stripping cables, frequently two V-shaped blades are used which cut into the cable insulation almost as far as the conductor. After the incision, the blades are moved back a small percentage of the insulation thickness. After this, the cable is retracted around the stripping path with the blades still delivered, or the blades execute the stripping path so that the blades strip the separated piece of insulation. In cable processing it is increasingly of great importance to be able to automatically detect production errors. As a result of the high requirement for the safety of electrical cables, for example, for the automobile or air travel industry, increasingly the smallest conductor breaches such as scratches or incisions are deemed to be a risk since these breaches together with the influence of vibration and/or corrosion can lead to rupture. Thus, some proposals have already been made to detect blade-conductor contact as is set out briefly hereinafter.

DE 10 2009 027967 A1 discloses a device for the detection of contact of an electrical conductor optionally encased by a mostly electrical insulation by a (stripping) tool which comprises a circuit arrangement connected to the tool and a tool consisting of electrically conductive material and electrically insulated with respect to the stripping device. In order to determine whether the blade contacts the conductor to be stripped, a voltage is applied to conductor or blade and it is merely determined whether a current flow takes place, which is brought about on contact of the conductor by the blade by closing the circuit which is formed. As long as no current flows, on the other hand, there is no mutual contact between the electrically conducting components blade and conductor. However, further methods of evaluation are not proposed. Thus, JP2133016A discloses the capacitive coupling of voltage onto the cable and the capacitive coupling of voltage out from the cable by means of an earthed blade as voltage stripper. The cable to be processed is guided before processing through two tube pieces functioning as electrodes. A high-frequency voltage is coupled capacitively into the cable through the first tube piece and coupled out capacitively in the second tube piece. If the earthed blade touches the conductor, this is identifiable as voltage drop at the second pipe piece. However, this method only functions for relatively short cables since long cables present a too-high capacitive load for capacitive coupling-in. On the other hand, the shortest cable length is given by the pipe lengths.

The inductive coupling-in of voltage onto the cable with capacitive coupling-out from the cable with an earthed blade as voltage stripper is the subject matter of the patent EP1772701B1. The cable to be processed is guided before processing through a toroidal coil and a pipe piece. A high-frequency voltage is coupled into the cable via the toroidal coil and coupled out via the pipe piece. If the earthed blade contacts the conductor, this is identifiable as a voltage drop at the second pipe piece. This method has the advantage that it only functions for relatively long, capacitively well-earthed cable and therefore can only be applied for one side of the stripping.

DE102007053825.3 and WO2012/015062A1 on the other hand describe the ohmic coupling of voltage onto the insulated blade. The stripping blade is fastened in an electrically insulated manner and connected via a resistance to a high-frequency voltage source. If the blade contacts the conductor, this can be identified as voltage drop or a change in voltage shape on the blade. In the case of short cables however, the ratio of the blade inherent capacitance to the cable capacitance is unfavourable and for this reason a detection of blade-conductor contact is expensive.

Combinations of the three methods explained above for detection of blade-conductor contact are described in JP7-227022A and JP2000354315A.

It is therefore the object of the present invention to provide a device which reliably, robustly and as simply as possible displays if a tool contacts an electrical conductor, which for example lies below an electrical insulation penetrated by the tool. In particular, it should be identified if at least one of the blades of a cable-stripping machine—or also its stripping tool—contacts the conductor—or in the case of a coaxial cable, the shielding. This detection of contact should also be possible for potential-free and short cable lengths, typically for cable lengths shorter than 80 mm when cutting in and when stripping the insulation.

The object is solved by the features of the independent patent claim 1 and the independent patent claim 16. Further advantageous features of embodiments according to the invention are contained in the dependent claims.

In the device for detecting contact of an electrical conductor encased by an electrical insulation by a tool which comprises a circuit arrangement connected to the tool, it is provided according to the invention that an inductance is connected between tool and tool holder and in such a manner that a high-Q parallel resonant circuit is built up between tool and tool holder and that a circuit arrangement for determining the change of characteristic oscillation parameters of this resonant circuit is connected to this. Typically the electrical conductor is part of a cable, either as central conductor under an electrically insulating sheath or in the form of a shielding of a coaxial cable. Stripping blades or stripping tools and also grippers or the like can be provided as tool. In contrast to known methods for detecting blade-conductor contact, these features according to the present invention offer the advantage that the central conductor of the cable to be stripped need not be electrically contacted and furthermore, the signal change for detecting the tool (in particular blade-)conductor contact is barely influenced by the conductor length, so that a quality control is possible, even with very short potential-free cables, with low expenditure of electronics.

This procedure differs significantly from all methods which are restricted to determining the closure of a circuit, such as for example DE 10 2009 027967 A1. These simple devices according to the prior art do not build up any kind of resonant circuits with the incorporation of elements of the stripping device and therefore also provide not determination of changes in characteristic oscillation parameters. Any capacitor arrangements provided remain unused in these known devices. The application of a voltage in order to be able to determine any current flow which may be present is a completely different principle from the structure according to the invention and the active operation of a parallel resonant circuit and the monitoring of its characteristic oscillation parameters.

Preferably the capacitance of the parallel resonant circuit is formed functionally by the arrangement of tool, insulation and tool holder. The tool and also the tool holder typically consist of electrically conductive material and both are galvanically separated from one another by a thin electrical insulation.

The capacitance of the parallel resonant circuit is also partially formed by the capacitance of the connection of tool and circuit arrangement, in particular by the capacitance of a coaxial cable.

If the capacitance determining the resonant circuit according to the above arrangements should be low for constructive reasons, in order to form a stable LC resonant circuit, the capacitance forming the resonant circuit can advantageously be increased by an output capacitor. This can also be advantageous when using a thicker insulation between tool and tool holder or when using a shorter coaxial cable.

In a simple and proven manner, at least one coil can be provided as inductance. Naturally other inductive components can also optionally be used within the framework of the invention.

Preferably the circuit arrangement has a frequency generator for an exciter voltage for the resonant circuit and a phase detector for evaluation of the phase shift between the exciter voltage and the resonant circuit voltage which is used to detect contact between tool and conductor. Thus, a relatively simple and reliable circuit can be achieved whose functionality is ensured even when a plurality of capacitances and/or inductances are switched in parallel.

A further advantageous embodiment of the invention is characterized in that the circuit arrangement has a device for evaluating the frequency response of the resonant circuit. A robust detection of a contact between the tool and the conductor is also thereby possible.

A further embodiment of the invention is characterized in that the circuit arrangement has a device for evaluating the shift of the resonance frequency of the resonant circuit. A robust method for determining contact of the electrical conductor by the tool is thereby possible.

Alternatively to the aforesaid embodiment, according to the invention the circuit arrangement can have a device for evaluating the change in the voltage amplitude of the resonant circuit.

A device for weighting is provided for the tool-conductor contacts during the cable processing according to contact time and specific time within the cable processing process, by which device quantitative production exclusion criteria can be determined.

Preferably the tool only abuts against a few, narrow locations on the tool holder and clearances are provided between these locations. The tool-tool holder capacitance can be reduced and therefore the capacitance ratio of conductor-earth to tool-tool holder can be increased by these openings. The sensitivity of the system is thereby increased.

According to a further embodiment according to the invention, the electrical insulation between tool and tool holder is formed by an electrically insulating coating of tool and/or tool holder, preferably by a ceramic coating. Typically tool and tool holder, for example, the blade and the tool holder of stripping machines are made of an electrically good-conducting material. The electrical insulation of blade to tool holder can then, for example, for a tool holder made of aluminium be accomplished by an ALTEF® coating.

Also at least one insulating intermediate disk can be provided between tool and tool holder, preferably at least one ceramic plate fastened, preferably adhesively bonded, on the tool or the tool holder. Scatterings of the capacitance such as can be caused, for example, by different coating thicknesses are thereby largely prevented. A particular advantages lies in the fact that the tool-ceramic-tool holder coating has a lower capacitance compared with an assembly having a substantially thinner coating. The sensitivity of the system can thus be increased and contacts of the tool on very thin conductor cross-sections can also be detected.

An additional embodiment of the invention provides that an encoder is provided for distance measurement between the tools and the circuit arrangement is designed for calculating the diameter of the conductor from the distance of the tools when a change in the oscillation parameter of the resonant circuit is determined.

Preferably a device according to the invention as described previously is characterized in that the tool is a stripping blade on a stripping machine for cable.

In order to solve the object formulated initially for a stripping machine which, having at least one stripping blade which is held on a tool holder and having a device for detecting the contact of an electrical conductor of a cable by at least one stripping blade, it is provided according to the invention that the stripping blade is the tool on the tool holder of a device according to any one of the preceding paragraphs.

The invention will be explained in detail by reference to an exemplary embodiment which is shown in the drawings. In the figures:

FIG. 1: shows the functional principle of the blade-conductor detection

Figure 2:
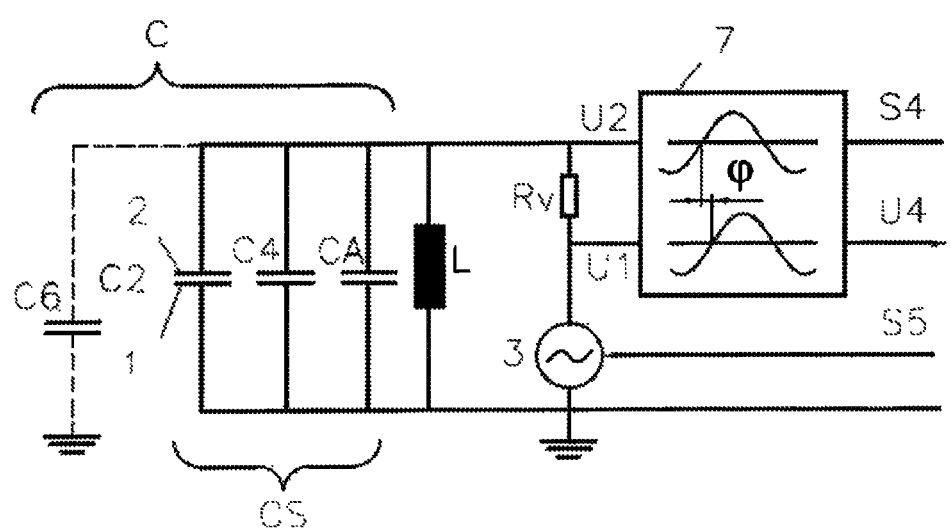

FIG. 2: shows the functional principle as a simplified electric diagram

Figure 3:
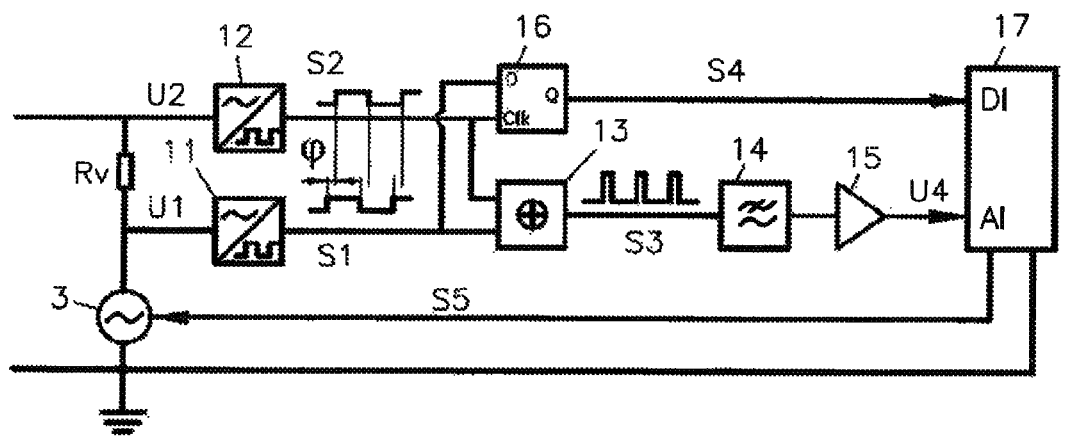

FIG. 3: shows a phase detector

Figure 4:
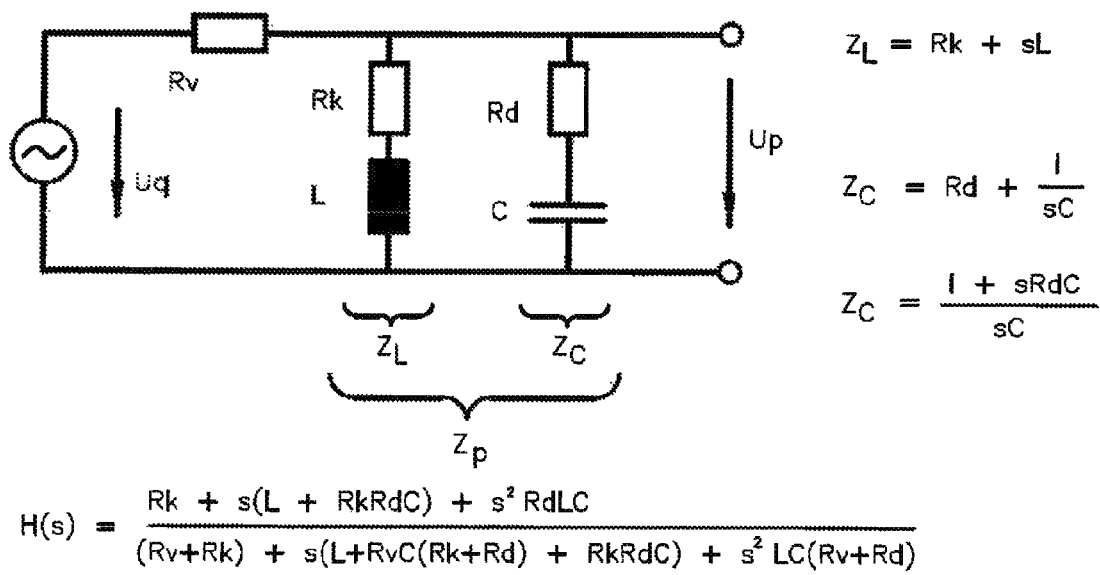
Figure 5:
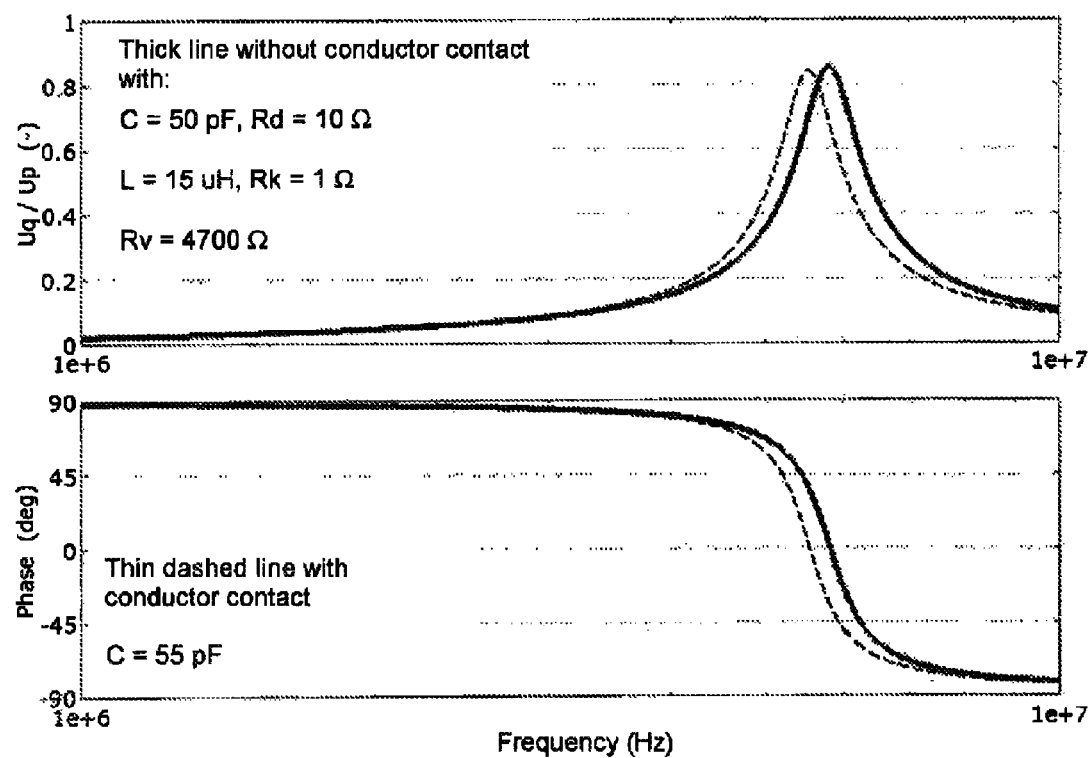
Figure 6:
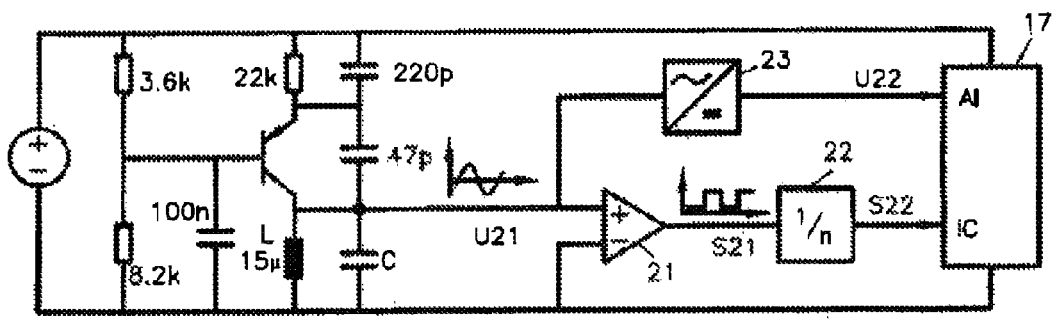
Figure 7:
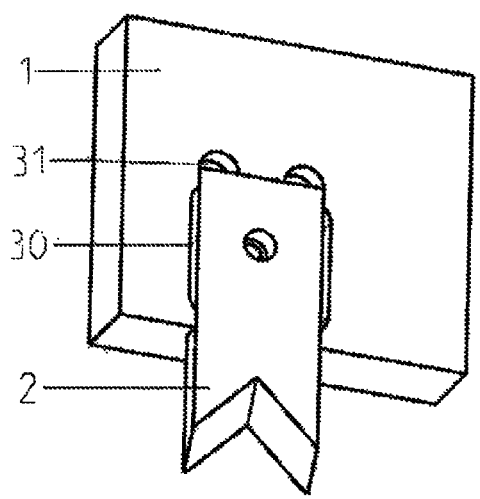
Figure 8:
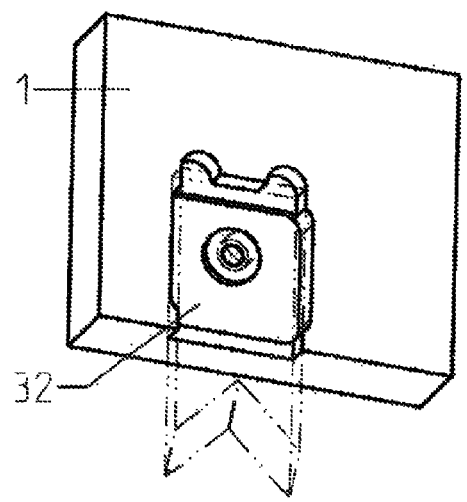
Figure 9:
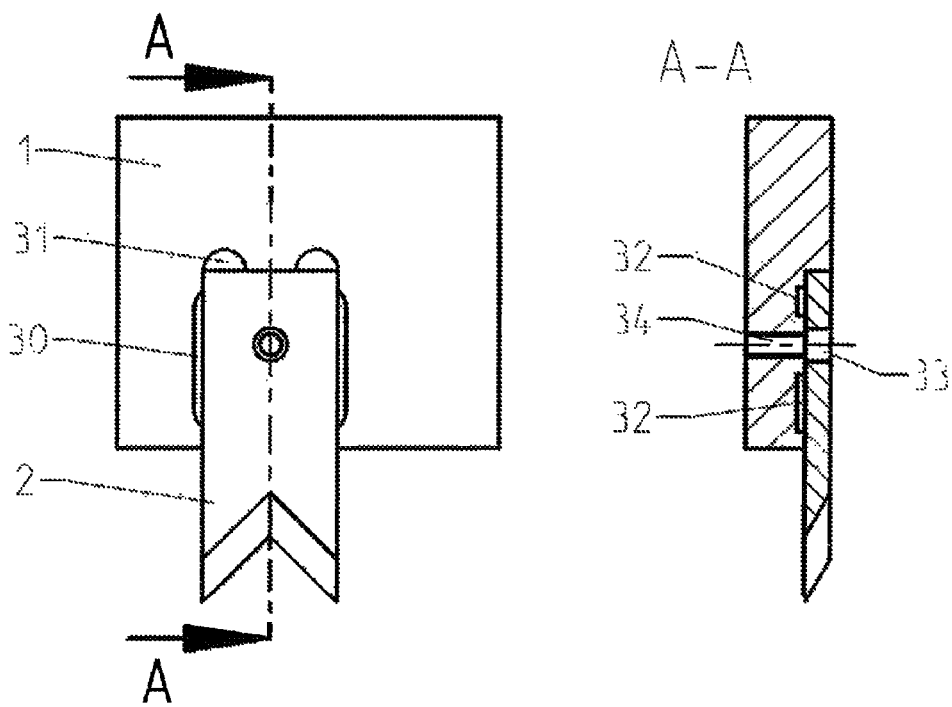
Figure 14:
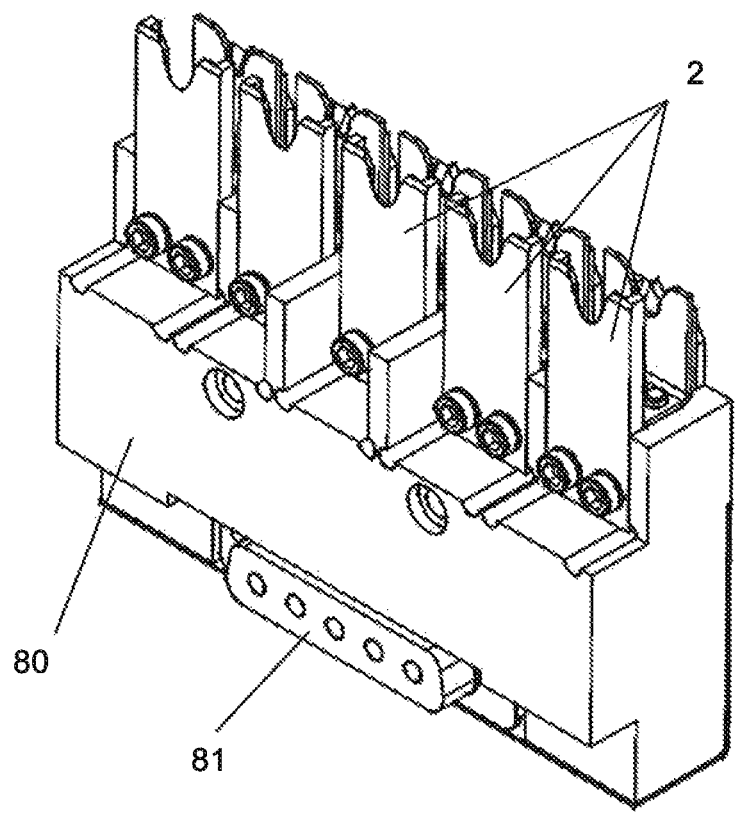

FIG. 4: shows an electrical equivalent circuit diagram and frequency response of the resonant circuit FIG. 5: shows a Bode diagram FIG. 6: shows an oscillator circuit FIG. 7: shows the blade on a tool holder, 3D view FIG. 8: shows a tool holder, 3D view FIG. 9: shows a view and section of the blade on the tool holder FIG. 10: shows a view and section of the blade on the tool holder with insulation FIG. 11: shows the determination of the conductor diameter FIG. 12: shows an exemplary embodiment of a blade contacting with contact piston in two views FIG. 13: shows an exemplary embodiment of a blade contacting with cable shoe FIG. 14: shows a blade beam with five separately operated blades FIG. 1 shows the functional diagram of the invention for the example of a blade-conductor contact detection for stripping machines for cables. The tool in the form of the blade $2a$ and its tool holder $1a$ as well as the blade $2b$ and the tool holder $1b$ are electrically separated from one another by a thin layer (not shown) and thus together form two plate capacitors. In the specific example a blade beam is provided as tool holder $1a$, $1b$. Instead of blades, grippers or similar devices can also be provided as tools. The electrical insulation can, for example, be achieved by means of an eloxide layer of a tool holder $1a$, $1b$ made of aluminium. Parallel to these capacitors, preferably in the immediate vicinity thereof, respectively one inductance La and Lb is attached so that a high-Q parallel resonant circuit, preferably having a Q factor greater than 5, is formed. This is excited by the oscillator 3, preferably part of a circuit arrangement, via the resistance Rv and the coaxial cable 4, at its resonance frequency. The oscillator voltage is preferably sinusoidal.

If one of the blades 2a or 2b contacts the electrical conductor 5b during the incision or stripping of the insulation 5as of the cable 5, the resonant circuit is detuned by the capacitance increase. The same also applies in the case of contact of an electrical conductor by another tool. The phase shift φ thereby formed between exciter voltage U1 and resonant circuit voltage U2 is transformed by a phase detector 7, also preferably part of the circuit arrangements, into an analogue voltage U4 and read in by a controller. The signal S4 is logic 1 when the voltage U1 is leading with respect to the voltage U2. The controller controls the oscillator 3 with signal S5 so that the resonant circuit is slightly leading with respect to the oscillator 3 in the open blade position, i.e. oscillates almost in self-resonance.

FIG. 2 shows the functional principle of FIG. 1 with the components shown there replaced by a simplified electric diagram. L is the total inductance formed from La and Lb. The second pole of the capacitor C2 is formed from the blades 2a, 2b and the first pole is formed from the tool holders 1a and 1b. Capacitor C4 represents the conductor capacitance of the coaxial cable 4 and CA an output capacitor of the electronics. The resonance frequency can be adjusted with the capacitance value of CA. The capacitor C6 represents the capacitance of the conductor 5b with respect to earth. In the event of a blade-conductor contact, the capacitance C6 is switched parallel to the capacitance C5. The total inductance C thus increases and detunes the LC resonant circuit. The functionality is also ensured if a plurality of blade-tool holder capacitances and a plurality of inductances are connected in parallel. The number of inductances need not agree with that of the blades. The total inductance can also be shifted locally into the vicinity of the series resistance Rv and the oscillator 3.

FIG. 3 shows an exemplary embodiment of a phase detector 7. The sinusoidal voltages U1 and U2 are transformed by the comparators 11 and 12 into the rectangular signals S1 and S2 which are linked to one another by an XOR component 13. In this case, the rectangular signal S3 is formed, the switch-on-period ratio of which is proportional to the phase shift φ between U1 and U2. The signal is filtered via the low-pass 14, amplified by the amplifier 15 and finally read in by the controller 17. The D flip-flop 16 generates the signal S4. This is logic 1 when S1 is leading with respect to S2, otherwise S4 is logic 0. By means of S4, the amplitude of U2 and possibly U4, the controller 17 which can also be part of the circuit arrangement, triggers the oscillator 3 so that the LC resonant circuit without conductor contact is slightly leading with respect to the oscillator 3, i.e. oscillates almost in self-resonance and consequently can respond sensitively to an increase in capacitance due to any conductor contact. If the resonant circuit is detuned by a conductor contact, the phase shift φ varies abruptly, the resonant circuit is trailing with respect to the oscillator 3 and therefore the D flip-flop output S4 is logic 1 and the processed cable 5 can be eliminated as reject.

FIG. 4 shows a differentiated equivalent circuit diagram and the frequency response of the resonant circuit derived from this for the theoretical analysis of the system. The capacitor and the inductance were expanded with their equivalent series resistances.

FIG. 5 shows the Bode diagram which shows the frequency response of the circuit from FIG. 4. Realistic values were used for the Bode diagram. The thick line shows the frequency behaviour without blade-conductor contact. The thin dashed line shows the frequency behaviour with blade-conductor contact. This contact was simulated by an increase in the total capacitance C from 50 to 55 pF since a small piece of cable which contacts the blade loads this capacitively with about 5 pF.

FIG. 6 shows a variant of an oscillator circuit. In contrast to the measurement principle described in FIG. 1 to FIG. 5 in which the frequency is fixed and the phase shift φ is measured, self-resonance is always established in the oscillator circuit shown here. The capacitance C represents the total capacitance and together with L forms the resonant circuit. The frequency and amplitude of the sinusoidal voltage U21 of the resonant circuit decrease when a conductor 5b contacts a tool 2a, 2b, for example, a blade. This results in two further methods for detecting a conductor contact: resonance frequency measurement and amplitude measurement.

For the resonance frequency measurement, U21 is transformed with a comparator 21 into a rectangular signal S21. The frequency of S21 is reduced by means of a frequency splitter 22. This results in the rectangular signal S22 whose frequency is measured by a controller 17. If one of the blades 2a, 2b contacts the conductor 5b, the frequency of S33 decreases abruptly. Although the frequency decrease by a conductor blade contact only accounts for a few percent, the method of resonance frequency measurement is very robust since the averaged frequency behaves stably without external influencing of the resonant circuit. Frequency drifts due to temperature changes can be taken into account with reference measurements in the open blade position.

For the amplitude measurement U21 is rectified with the rectifier 23. This results in an analogue voltage signal U22 which can be evaluated by the controller 17. The rectification can be made, for example, using an analogue multiplier whereby U21 is multiplied by itself and then filtered with a lowpass. However a simple peak-value rectifier, a Greinacher or a Delon circuit can also be used as rectifier. Amplitude drifts due to temperature changes can be taken into account with reference measurements in the open blade position.

FIG. 7, FIG. 8 and FIG. 9 show a variant of the blade mounting in the tool holder 1. The blade is fixed positively with a screw on the tool holder through the hole 33 in the blade 2 and thread 34 in the tool holder 1. At the side and on the base surface, the blade only rests where it is required to transmit the cutting, stripping and fastening forces. The blade-tool holder capacitance can be reduced with the openings 30, 31, and 32 in the tool holder. As a result the conductor-earth to blade-tool holder capacitance ratio is increased and the sensitivity of the system is increased.

The blades 2a, 2b and the tool holders 1a, 1b are made of an electrically good-conducting material. The electrical insulation of blades 2a, 2b to tool holders 1a, 1b is achieved by making the tool holder, e.g. of aluminium and coating with an ALTEF® layer. The very hard ALTEF® layer is particularly abrasion-proof, corrosion-resistant, non-stick and has a low coefficient of friction. The surface of the base material is thereby converted into a ceramic layer in which Teflon® is embedded. Half the layer thickness grows into the base material. Naturally, differently configured ceramic plates or ceramic elements can also be inserted between the blades 2a, 2b and the respective tool holder 1a, 1b and connected to these components, which can preferably be achieved by adhesive bonding. Preferably for example a 1.5 mm thick ceramic is applied to both sides of the tool holder and adhesively bonded to the tool and only then finished as a compound product, whereby precise fit sizes can be achieved. Furthermore, such a ceramic plate is also very wear-resistant and insensitive during handling, for example, when changing the tool.

The specific configuration will naturally take into account the manufacturing process for ceramic-coated components. The complete insulation therefore preferably consists of a plurality of ready-to-manufacture components as well as advantageously the tool holders will also consist of a plurality of individual parts. The insulation between tool and tool holders in this case covers all joining surfaces.

FIG. 10 shows a further variant of the blade mounting whereby the blade-tool holder capacitance can be further reduced by an insulating intermediate disk 40.

Depending on the cable 5 and processing process, it can be appropriate for the detection of blade-conductor contact if along with or instead of a fixed threshold value for the phase shift φ, a standard band of the phase shift is specified as a function of time or the progress of the process. If the phase shift φ during the processing cycle falls outside this standard band, the cable 5 can be eliminated as reject.

As a result of the exact detection of contact between tool 2a, 2b and conductor 5b, it is possible to measure the diameter d of the conductor 5b. Hitherto, this was only possible for example with blades 2a, 2b by means of the difficult-to-detect increase in force of the cutting force in the case of blade-conductor contact.

FIG. 11 shows the geometrical relationships of the two V-shaped blades 2a, 2b during the process of cutting into the insulation 5a at the time of blade-conductor contact. An ideal cutting process is assumed here: the cable 5 has a symmetrical structure and the blade cutting edges penetrate symmetrically into the insulation 5a so that preferably the first blade-conductor contact takes place simultaneously at all four cutting edges.

At the time of the blade-conductor contact, an encoder measures the blade opening x. Together with the opening angle α the conductor diameter d can thus be calculated using the following formula:

$$d = x \cdot \sin\left(\frac{\alpha}{2}\right)$$

For standard blades 2a, 2b having an opening angle of 90°, we thus have:

$$d = \frac{x}{\sqrt{2}}$$

It should be mentioned that the determination of the conductor diameter is also possible for non-insulated conductors and is not only restricted to v-shaped blades; guillotine blades or similar are also feasible for determination of the conductor diameter.

FIG. 12 shows an exemplary embodiment of how the blade 2a is electrically connected to the internal conductor 57 of a coaxial cable 4. The blade 2a is fastened to a blade cassette 52 using a screw 50 via an electrically insulating washer 51. The blade cassette 52 has an electrically insulating coating on the contact surface 52a to the blade 2a. The blade cassette 52 is screwed onto the blade beam 53 in an electrically conducting manner. Blade cassette 52 and blade beam 53 in the exemplary embodiment shown jointly form the tool holder 1. Located in the blade beam 53 is a groove 54 into which the coaxial cable 4 is laid, its shielding 55 being connected electrically to the blade beam 53 by means of a shielding clamping plate 56. The internal conductor 57 of the coaxial cable 4 is soldered onto the contact piston 58. The contact piston 58 is mounted by means of an insulating bush 59 which is pressed into the blade beam 53. The contact force of the contact piston 58 onto the blade 2a is given by the pre-tensioning of the O-ring 60. A securing ring 61 ensures that the contact piston 58 is axially fixed so that this remains in place even when the blade cassette 53 is removed or the blades 2a, 2b are removed.

FIG. 13 shows another exemplary embodiment of how the blade 2 is electrically connected to the internal conductor 57 of the coaxial cable 4. Blade 2 is screwed onto the blade holder 1 by means of a screw 50 via two electrically conducting washers 71 and a cable shoe 70. The cable shoe 70 is made from a double-sided printed circuit board. The shielding 55 of the coaxial cable 4 is soldered onto the copper surfaces 70a and 70b which are electrically connected to one another by the vias 70c. The internal conductor 57 of the coaxial cable 4 is soldered onto the copper surface 70d.

FIG. 14 shows a design of a blade beam 80 with specifically five adjacent blades 2 which can each be evaluated separately and in pairs according to the above-described principle according to the invention. Preferably however for simpler and more rapid handling, the coaxial cable (not shown) for each resonant circuit is guided to a common plug 81. A contacting print (not visible) with a coil L for the resonant circuit is inserted between each of the blades 2 and the blade beam 80. The capacitance C of the resonant circuit is formed according to one of the variants already described above.

Finally it should also be mentioned that the device according to the invention functions similarly with all types of blades for stripping machines whether these are centrally closing blades, guillotine blades, rotating blades, iris diaphragm blades or the like.

REFERENCE LIST 1a, 1b Tool holder
2a, 2b Tool
3 Frequency generator (oscillator)
4 Coaxial cable
5 Insulation of the conductor
5b Electrical conductor
7 Phase detector
11, 12 Comparators
13 XOR component
14 Lowpass
15 Amplifier
16 D flip-flop
17 Controller
21 Comparator
22 Frequency splitter
23 Rectifier
30,31,32 Openings
33 Hole
34 Thread
40 Intermediate disk
50 Screw
51 Washer
52 Blade cassette
52a Contact surface
53 Blade beam 54 Groove
55 Shielding of coaxial cable
56 Shielding clamping plate
57 Internal conductor of coaxial cable
58 Contact piston
59 Insulating bush
60 O ring
61 Securing ring
70 Cable shoe
70a,70b Copper surfaces
70d
70c Vias
71 Washers
80 Blade beam
81 Plug
82 Contacting print
C,C2,C4 Capacitances
C6
CA Output capacitor
L Coil, inductance
La, Lb Inductances

The invention claimed is:

1. A device for detecting contact of an electrical conductor (5b), which is encased by electrical insulation (5a), by a tool (2a; 2b) which comprises an electrically conductive material, and which is fastened to a tool holder (1a; 1b) made of electrically conductive material, wherein a thin electrical insulation is provided between the tool and the tool holder, an inductance (La; Lb) is connected between the tool (2a; 2b) and the tool holder (1a; 1b) such that a high-Q parallel resonant circuit is built up between the tool (2a, 2b) and the tool holder (1a, 1b) and that a circuit arrangement (3, 7) for determining a change of characteristic oscillation parameters of the high-Q parallel resonant circuit is connected to the tool.

2. The device according to claim 1, wherein a capacitance (C2) of the high-Q parallel resonant circuit is formed functionally by an arrangement of the tool (2a, 2b), the thin electrical insulation and the tool holder (1a, 1b).

3. The device according to claim 1, wherein a capacitance (C4) of the high-Q parallel resonant circuit is formed either by a capacitance of the connection of the tool (2a, 2b) and the circuit arrangement (3, 7) or by a capacitance of a coaxial cable (4).

4. The device according to claim 1, wherein a capacitance (CS) forming the high-Q parallel resonant circuit is at least partially increased by an output capacitor (CA).

5. The device according to claim 1, wherein at least one coil (L) is provided as the inductance (La, Lb).

6. The device according to claim 1, wherein the circuit arrangement has a frequency generator (3) for an exciter voltage for the high-Q parallel resonant circuit and a phase detector (7; 11-16) for evaluation of a phase shift φ between the exciter voltage and a voltage of the high-Q parallel resonant circuit.

7. The device according to claim 1, wherein the circuit arrangement (3, 7) has a device for evaluating a frequency response of the high-Q parallel resonant circuit.

8. The device according to claim 1, wherein the circuit arrangement has a device (21, 22) for evaluating a shift of a resonance frequency of the high-Q parallel resonant circuit.

9. The device according to claim 1, wherein the circuit arrangement has a device (23) for evaluating a change in a voltage amplitude of the high-Q parallel resonant circuit.

10. The device according to claim 1, wherein a device for weighting is provided for tool-conductor contacts during cable processing according to contact time and a specific time within a cable processing process, by which device quantitative production exclusion criteria can be determined.

11. The device according to claim 1, wherein tool (2a, 2b) only abuts against a few, narrow locations on the tool holder (1a, 1b) and clearances (30, 31 and 32) are provided between the narrow locations on the tool holder.

12. The device according to claim 1, wherein the thin electrical insulation between the tool (2a, 2b) and the tool holder (1a, 1b) is formed by an electrically insulating ceramic coating of at least one of tool and the tool holder.

13. The device according to claim 1, wherein at least one insulating intermediate disk (40) is provided between the tool (2a, 2b) and the tool holder (1a, 1b), the insulating intermediate disk comprising at least one ceramic plate that is adhesively bonded on either the tool or the tool holder.

14. The device according to claim 1, wherein an encoder is provided for distance measurement between the tools (2a, 2b) and the circuit arrangement is designed for calculating a diameter of the electrical conductor (5b) from a distance of the tools (2a, 2b) when the change in the oscillation parameter of the high-Q parallel resonant circuit is determined.

15. The device according to claim 1, wherein the tool is a stripping blade (2a, 2b) on a stripping machine for cable (5).

16. A stripping machine comprising at least one stripping blade (2a, 2b) which is held on a tool holder (1a, 1b) and comprising a device for detecting contact of an electrical conductor (5b) of a cable (5), which is encased by electrical insulation (5a), by at least one of the stripping blades, the stripping blade comprises an electrically conductive material and is fastened to the tool holder (1a; 1b) which made of electrically conductive material, a thin electrical insulation is provided between the stripping blade and the tool holder, an inductance (La; Lb) is connected between the stripping blade (2a; 2b) and the tool holder (1a; 1b) such that a high-Q parallel resonant circuit is built up between the stripping blade (2a, 2b) and the tool holder (1a, 1b) and that a circuit arrangement (3, 7) for determining a change of characteristic oscillation parameters of the high-Q parallel resonant circuit is connected to the stripping blade.

* * * * *